United States Patent
Becker et al.

(10) Patent No.: US 11,975,145 B2
(45) Date of Patent: May 7, 2024

(54) ENDO-TRACHEAL CATHETER FOR USE IN AN ANESTHETIC PROCEDURE

(71) Applicant: Fresenius Kabi Deutschland GmbH, Bad Homburg (DE)

(72) Inventors: Michael Becker, Knittlingen (DE); Dieter Pruss, Scharbeutz (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 753 days.

(21) Appl. No.: 16/648,619

(22) PCT Filed: Sep. 7, 2018

(86) PCT No.: PCT/EP2018/074140
§ 371 (c)(1),
(2) Date: Mar. 18, 2020

(87) PCT Pub. No.: WO2019/057520
PCT Pub. Date: Mar. 28, 2019

(65) Prior Publication Data
US 2020/0222650 A1 Jul. 16, 2020

(30) Foreign Application Priority Data
Sep. 20, 2017 (EP) ..................................... 17192049

(51) Int. Cl.
*A61M 16/04* (2006.01)
*A61M 16/08* (2006.01)

(52) U.S. Cl.
CPC .... *A61M 16/0463* (2013.01); *A61M 16/0833* (2014.02); *A61M 16/085* (2014.02); *A61M 2202/048* (2013.01); *A61M 2230/437* (2013.01)

(58) Field of Classification Search
CPC .......... A61M 16/0463; A61M 16/0833; A61M 16/085; A61M 2202/048; A61M 2230/437
See application file for complete search history.

(56) References Cited

U.S. PATENT DOCUMENTS

| 4,805,611 A | 2/1989 | Hodgkins |
| 4,815,459 A * | 3/1989 | Beran ................... A61B 5/097 128/207.14 |

(Continued)

FOREIGN PATENT DOCUMENTS

| WO | WO-2005067986 A1 * | 7/2005 | ........... A61L 2/0094 |

OTHER PUBLICATIONS

International Search Report and Written Opinion for International Application No. PCT/EP2018/074140 dated Nov. 28, 2018.

*Primary Examiner* — Elliot S Ruddie
*Assistant Examiner* — Maap Ahmed Ellabib
(74) *Attorney, Agent, or Firm* — Cook Alex Ltd.

(57) ABSTRACT

An endo-tracheal catheter for use in an anesthetic procedure comprises a catheter tube to be inserted into the trachea of a patient, the catheter tube having a tubular wall defining an inner lumen for guiding a gaseous flow, and a connection piece which defines a chamber in fluid connection with the catheter tube and comprising a port for connecting a detection device to the endo-tracheal catheter for detecting at least one substance in the gaseous flow flowing through the catheter tube. An insert tube is received in the inner lumen of the catheter tube for guiding the gaseous flow through the catheter tube and/or a coating covers the tubular wall at a side facing the inner lumen for guiding the gaseous flow through the catheter tube.

16 Claims, 2 Drawing Sheets

(56) References Cited

U.S. PATENT DOCUMENTS

| | | | |
|---|---|---|---|
| 5,830,185 A | 11/1998 | Block, Jr. | |
| 2004/0231675 A1* | 11/2004 | Lyons | A61M 16/042 |
| | | | 128/207.18 |
| 2011/0023888 A1* | 2/2011 | Vazales | A61B 1/00142 |
| | | | 128/207.14 |
| 2012/0136272 A1 | 5/2012 | Varis et al. | |
| 2014/0018691 A1 | 1/2014 | McNeill | |
| 2014/0150782 A1* | 6/2014 | Vazales | A61M 25/1018 |
| | | | 128/202.16 |
| 2014/0238398 A1* | 8/2014 | Christopher | A61B 5/087 |
| | | | 128/204.22 |
| 2015/0297800 A1* | 10/2015 | Weikart | A61J 1/05 |
| | | | 422/430 |
| 2015/0320971 A1* | 11/2015 | Leeflang | A61L 29/14 |
| | | | 427/2.3 |
| 2015/0343182 A1 | 12/2015 | Vazales et al. | |
| 2016/0296719 A1* | 10/2016 | Geraghty | A61M 16/085 |

\* cited by examiner

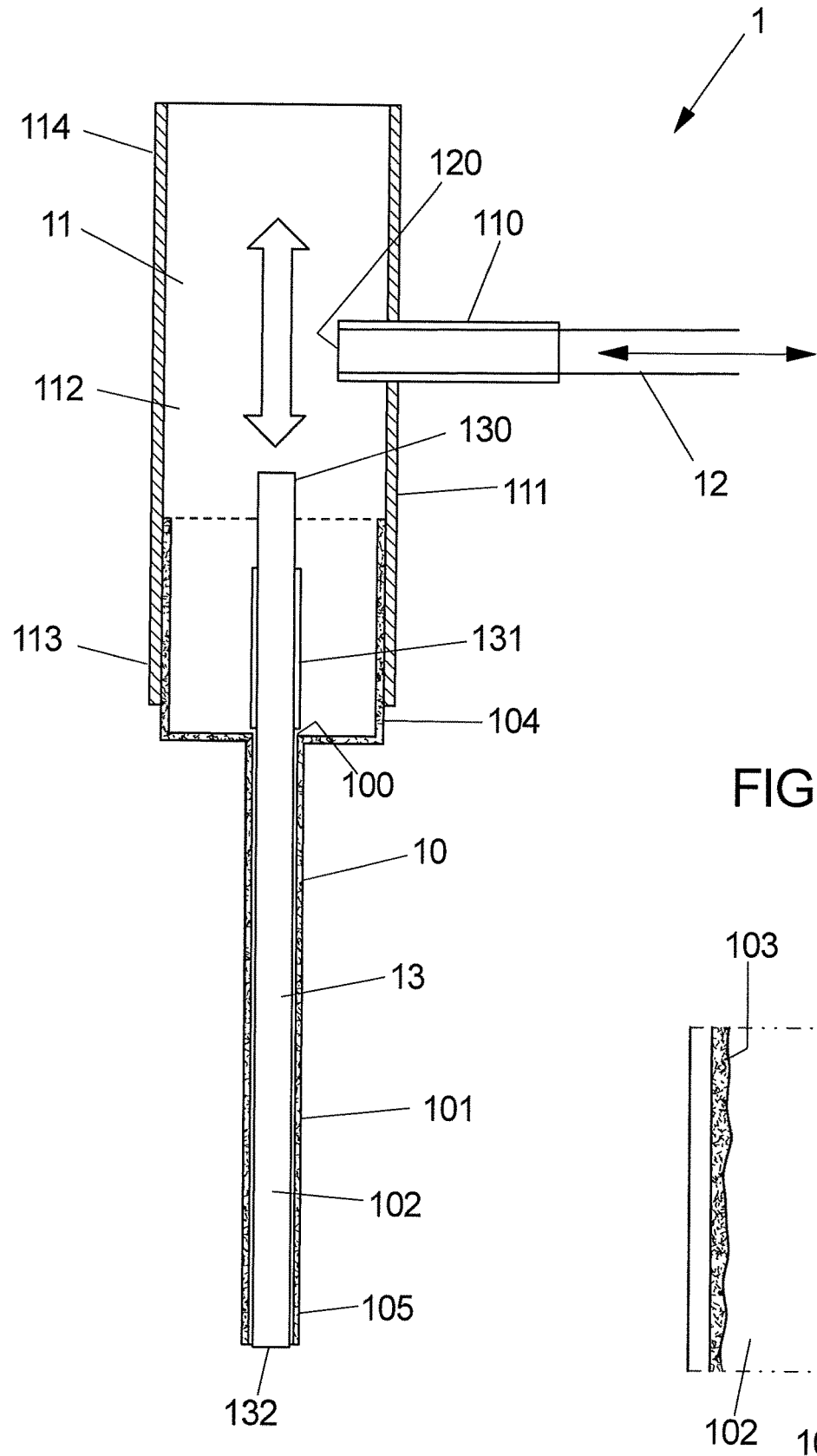

ENDO-TRACHEAL CATHETER FOR USE IN AN ANESTHETIC PROCEDURE

CROSS REFERENCE TO RELATED APPLICATIONS

The present application is a U.S. National Stage of PCT International Patent Application No. PCT/EP2018/07 4140, filed Sep. 7, 2018, which claims priority to EP Application No. 17192049.9, filed Sep. 20, 2017, both of which are hereby incorporated herein by reference.

FIELD OF THE INVENTION

The invention relates to an endo-tracheal catheter for use in an anesthetic procedure according to the preamble of claim 1.

An endo-tracheal catheter of this kind comprises a catheter tube to be inserted into the trachea of a patient, the catheter tube having a tubular wall defining an inner lumen for guiding a gaseous flow. A connection piece defines a chamber which is in fluid connection with the catheter tube and comprises a port for connecting a detection device to the endo-tracheal catheter for detecting at least one substance in the gaseous flow flowing through the catheter tube.

In conventional general anesthesia procedures mechanical ventilation is used, for example in an operating center or during long-term sedation procedures for critically ill patients in an intensive care unit of a hospital. In the context of such general anesthesia procedures patients are intubated with endo-tracheal catheters to on the one hand provide for a ventilation and on the other hand administer gaseous anesthetic agents.

As an alternative to inhalational anesthesia procedures using gaseous anesthetic agents, in the context of intravenous anesthesia an anesthetic agent such as Propofol is administered intravenously into a patient, for example in the context of a so-called total intravenous anesthesia (TIVA) procedure. Such intravenous anesthesia may be preferable for example for a long-term sedation procedure in an intensive care unit.

In particular in the context of intravenous anesthesia for example using Propofol as an anesthetic agent, it is of substantial interest to be able to monitor the concentration of the anesthetic agent in the patient's body and its related effects in particular with regard to the anesthetic impact. Generally, conclusions with regard to the drug concentration in the patient's body can be drawn by monitoring the presence and concentration of an anesthetic agent and related substances in the exhaled air of a patient. Using a suitable modeling, for example a pharmacokinetic/pharmacodynamic model, the drug concentration in the patient's body can be predicted from the drug concentration in the exhaled air, such predictions however requiring on the one hand precise models and on the other hand a precise measuring of substance concentration in the exhaled air.

Standard catheter tubes may for example be made from a polyvinyl chloride (PVC) material, which allows for a cost-effective production of catheter tubes, in particular for endo-tracheal catheters. However, a catheter tube made from a PVC material may exhibit a substantial adhesion for anesthetic agents, in particular Propofol, causing molecules to be adsorbed on the PVC tube wall and hence having an effect on the measurement of the substance concentration in the exhaled breath of a patient. Generally, adsorption effects are strongest immediately after the start of a measurement procedure due to a strong adsorption on the catheter tube and may decrease until an equilibrium of adsorption and desorption of molecules on the tube wall is reached. Generally, adsorption of molecules may cause a delay and a reduction in signal strength, potentially leading to inaccurate concentration measurements in the exhaled air.

It is an object of the instant invention to provide an endo-tracheal catheter allowing for an accurate measurement of a substance concentration in a gaseous flow, in particular in the context of an anesthesia procedure.

This object is achieved by means of an endo-tracheal catheter comprising the features of claim 1.

Accordingly, an insert tube is received in the inner lumen of the catheter tube for guiding the gaseous flow through the catheter tube and/or a coating covers the tubular wall at a side facing the inner lumen for guiding the gaseous flow through the catheter tube.

Within the inner lumen of the catheter tube, hence, an insert tube is received, or a coating covers the tubular wall defining the inner lumen. In each case, the tubular wall, at its inside, is covered (by the insert tube respectively the coating) such that a direct contact of the gaseous flow with the tubular wall is prevented.

Because the insert tube and/or the coating prevent the gaseous flow—and hence also anesthetic agents or substances relating to anesthetic agents present in the gaseous flow—to come into direct contact with the tubular wall, the tubular wall may be produced from a material such as polyvinyl chloride (PVC), having characteristics of substantial adsorption for anesthetic agents such as Propofol, but allowing for a cheap production of the tubular wall and hence the catheter tube. Because molecules of the anesthetic agent or substances relating to the anesthetic agent do not come into contact with the tubular wall, the adsorption characteristics of the tubular wall do not impact concentration measurements of the anesthetic agent or substances relating to the anesthetic agent.

In particular, the insert tube and/or the coating may be made from a material different than the tubular wall of the catheter tube and in particular may be made from a material providing for a reduced adhesion—as compared to the tubular wall of the catheter tube—of a substance of interest, in particular an anesthetic agent, to be detected by means of the detection device to be connected to the connection piece of the endo-tracheal catheter.

Generally, an insert tube (received in the inner lumen and beneficially extending through the inner lumen from a first end of the catheter tube connected to the connection piece to a second, far end of the catheter tube to be inserted into the trachea of a patient) and a coating covering the tubular wall at its inside may be used as alternatives, but may also be used in combination. In the latter case, a coating may cover the tubular wall at its inside, wherein in addition an insert tube is received in the inner lumen of the catheter tube.

A coating, in addition or alternatively to a coating on the tubular wall of the catheter tube, may be placed on the insert tube to cover the insert tube at its inside.

The insert tube may for example be made from or may comprise a material such as PTFE (polytetrafluoroethylene), PFA (perfluoralkoxy polymer), FEP (perfluor(ethylene-propylene)), or PEEK (polyether ether ketone), i.e., a material generally exhibiting reduced adsorption characteristics in particular for an anesthetic agent such as Propofol.

The insert tube is received within the inner lumen of the catheter tube and prevents the gaseous flow flowing through the insert tube to come into direct contact with the tubular wall of the catheter tube. The insert tube comprises a tubular flow channel for guiding the gaseous flow through the catheter tube such that the gaseous flow is guided through the insert tube. To avoid a substantial reduction of the cross-sectional area of the catheter tube for guiding the gaseous flow, the insert tube beneficially has a small wall thickness, for example a wall thickness of 0.5 mm or less, such that the insert tube essentially does not reduce the inner diameter of the catheter flow channel.

In one embodiment, the insert tube comprises a proximal end reaching into the chamber and protruding from a catheter tube opening of the catheter tube at which the catheter tube opens into the chamber of the connection piece. The insert tube hence extends beyond the tubular wall of the catheter tube into the chamber, beneficially towards the port of the connection piece to which the detection device may be connected for detecting the substance of interest in the gaseous flow flowing through the catheter tube.

In one embodiment, the tubular flow channel of the insert tube opens into the chamber at a location in the vicinity of the port, such that via the port a probe of the gaseous flow may be taken essentially without the gaseous probe coming into contact with housing walls of the connection piece, but being drawn directly into the port for detection by means of the detection device.

The insert tube may be releasably received in the inner lumen of the catheter tube. For example, a set of different insert tubes may exist and may be provided by the manufacturer to be used in combination with different catheter tubes, for example catheter tubes having different lengths and different diameters. To configure an endo-tracheal catheter for use for example in the context of an anesthetic procedure, a user, for example a nurse, may equip the catheter tube with a suitable insert tube by inserting the insert tube into the catheter tube such that the insert tube is received within the inner lumen of the catheter tube. When received in the inner lumen of the catheter tube, the insert tube beneficially covers the inside of the tubular wall of the catheter tube and for this is in close abutment with the tubular wall.

The insert tube may be inserted into the catheter tube via the end of the catheter tube associated with the connection piece. In order to axially secure the insert tube with respect to the catheter tube, in particular to prevent the insert tube to fully move into the catheter tube, a stop element is placed on the proximal end of the insert tube, for example in the shape of a sleeve circumferentially encompassing the proximal end of the insert tube. The stop element is axially fixed on the proximal end of the insert tube and has dimensions larger than the diameter of the inner lumen of the catheter tube such that the stop element may not move into the inner lumen and hence prevents an axial movement of the insert tube with respect to the catheter tube.

If a coating, in addition to or alternatively to an insert tube, is used on the inside of the tubular wall defining the inner lumen of the catheter tube, such coating may for example be made from a sapphire (SiOx) material having a very small thickness, for example in the range of a view micrometers, for example less than 10 µm, preferably less than 5 µm. The coating prevents a direct contact of the gaseous flow with the tubular wall of the catheter tube such that adsorption of a substance of interest on the tubular wall is prevented. Due to its small thickness, the coating essentially does not have an impact on the tube's flexibility.

A coating of this kind may also be used on the inside of a housing wall of the connection piece such that the gaseous flow may not directly come into contact with the housing wall of the connection piece.

The catheter tube terminates at the connection piece, which by means of its port allows for a connection of a detection device—in particular a gas detector suitable to detect a substance of interest in the gaseous flow—to the endo-tracheal catheter. For connecting a detection device to the connection piece, a side-stream line may be mounted on the port connecting the endo-tracheal catheter to the detection device.

In one embodiment, the side-stream line reaches into the chamber of the connection piece and protrudes from a housing wall of the connection piece towards the inside of the chamber. The side-stream line hence reaches into the chamber, preferably towards a central axis of the connection piece along which a mainstream of the gaseous flow flows during operation of the endo-tracheal catheter. If a tip of the side-stream line in particular is placed close to the proximal end of the insert tube, a gas probe may be drawn from the gaseous flow without coming into contact with housing walls of the connection piece, such that effects on the gaseous probe by adsorption on the housing walls of the connection piece is avoided or at least substantially reduced.

In one embodiment, the side-stream line is made from a comprises a material such as PTFE, PFA, FEP, or PEEK. In addition or alternatively, the side-stream line may comprise a coating such as a thin sapphire (SiOx) layer. By these means adsorption on the side-stream line may additionally be avoided or at least substantially reduced.

A coating of the kind described herein may be formed on the tubular wall of the catheter tube or on the side-stream line connecting the connection piece to a detection device by deposition of a suitable material, for example a sapphire (SiOx) layer, on the tubular wall respectively the side-stream line, such that a thin coating layer is formed on the inside of the tubular wall of the catheter tube or on the inside of the side-stream line.

Alternatively, a coating may be formed by manufacturing the catheter tube and/or the side-stream line by using a co-extrusion process in which the catheter tube respectively the side-stream line are formed as a multi-layered tube from two or more different materials. In this way the catheter tube and/or the side-stream line may on the outside have a material layer formed for example from PVC and on the inside have a layer formed from another material which in particular exhibits characteristics of reduced adhesion of a substance of interest, in particular an anesthetic agent, to be detected by means of the detection device to be connected to the connection piece of the endo-tracheal catheter. The inner layer of the catheter tube and/or the side-stream line may in particular be formed from or may comprise a material such as PTFE (polytetrafluoroethylene), PFA (perfluoralkoxy polymer), FEP (perfluor(ethylene-propylene)), or PEEK (polyether ether ketone), i.e., a material generally exhibiting reduced adsorption characteristics in particular for an anesthetic agent such as Propofol. The catheter tube and/or the side-stream line hence are formed as tubes having multiple wall layers, an inner wall layer providing for a reduced adhesion of a substance of interest, in particular an anesthetic agent to be detected by means of the detection device to be connected to the connection piece of the endo-tracheal catheter.

An endo-tracheal catheter of this kind may in particular be used within a system suitable for being used in the context of an anesthesia procedure. Such system may in particular comprise a ventilation system allowing for a ventilation of a patient, the ventilation system having a ventilator attached to the connection piece of the endo-tracheal catheter.

The idea underlying the invention shall subsequently be described in more detail with reference to the embodiments shown in the drawings. Herein:

FIG. 2 shows a schematic view of an embodiment of an endo-tracheal catheter; and FIG. 3 shows a schematic view of a catheter tube of an endo-tracheal catheter comprising a coating.

FIG. 1 shows an embodiment of a system as it generally may be used for example in the context of an anesthesia procedure.

Figure 1:
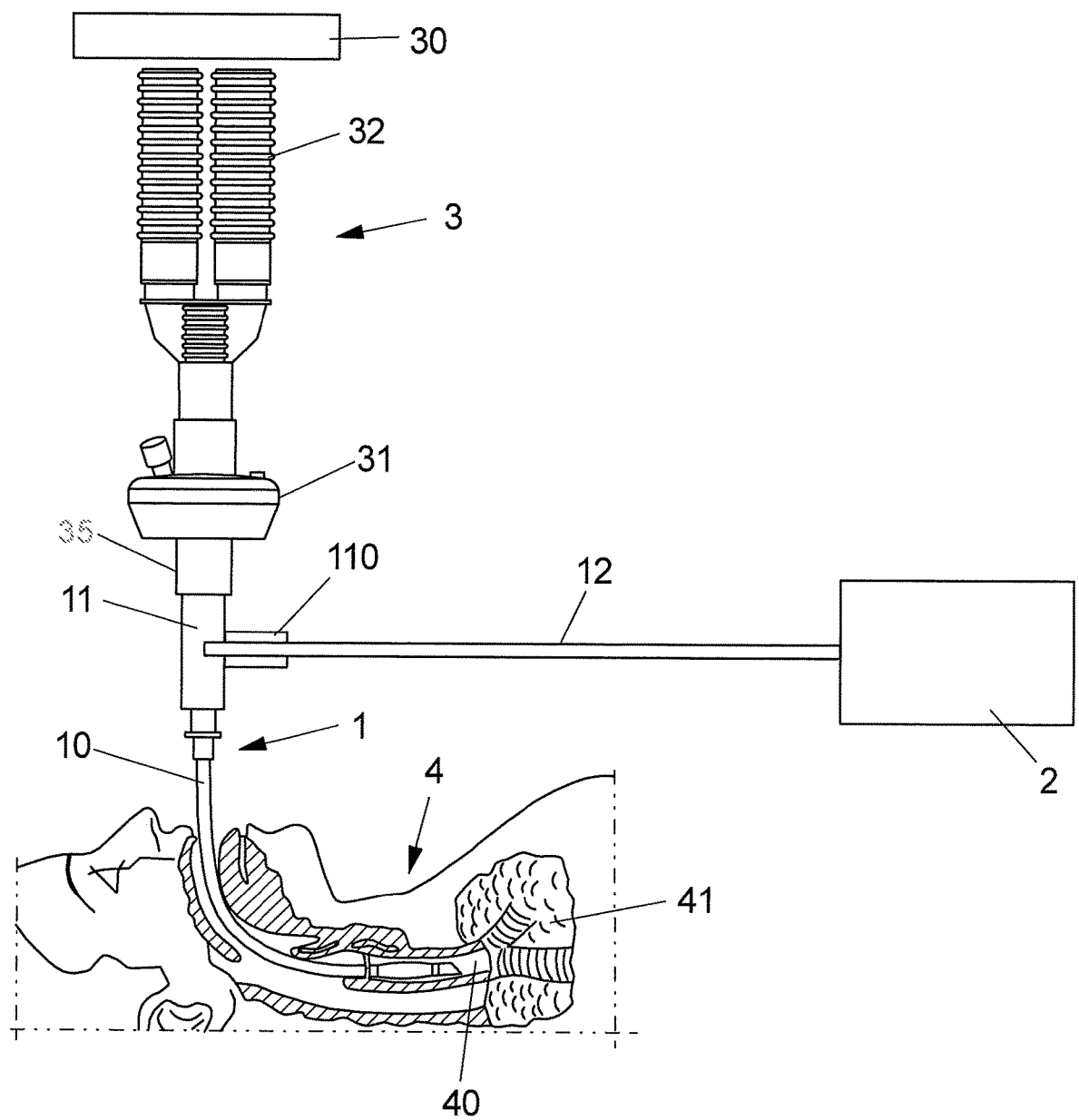
FIG. 1 shows a schematic view of a system comprising an endo-tracheal catheter and a ventilation system for providing ventilation to a patient.

For example in an intravenous anesthesia procedure, an anesthetic agent such as Propofol is intravenously administered to a patient 4 and hence enters into the patient's bloodstream. In order to monitor the concentration of the anesthetic substance within the patient's body, a gas detector 2 connected to a connection piece 11 of an endo-tracheal catheter 1 continuously or periodically measures a drug concentration in a gaseous flow taken from the patient's lungs 41 via a catheter tube 10 of the endo-tracheal catheter 1 inserted into the trachea 40 of the patient 4. By means of such concentration measurements, hence, a monitoring of the substance concentration in the exhaled air of the patient 4 may be conducted, allowing for conclusions with respect to the concentration of the anesthetic substance within the patient's body, for example using a suitable pharmacokinetic/pharmacodynamic model or the like.

By means of the system also a ventilation to the patient 4 may be provided. For this, a ventilation system 3 is connected to the connection piece 11 of the endo-tracheal catheter 1. The ventilation system 3 comprises a ventilator 30 for providing ventilation via ventilation lines 32 and a filter 31 connected to the connection piece 11 via a connector 35. The filter 31 in particular serves to protect the ventilator 30 against contamination and moisture.

Generally, molecules of an anesthetic agent or a substance relating to an anesthetic agent may be subject to adsorption on the tubular wall of the catheter tube 10. Such adsorption may be strongest at the beginning of a measurement procedure, potentially having a substantial impact on measurement results for measuring the concentration of the anesthetic agent or substances relating to the anesthetic agent within the gaseous flow guided via the catheter tube 10. Such adsorption effects may vary over time and may cause a substantial deterioration of accuracy in the concentration measurements.

In order to at least reduce effects of adsorption of a substance of interest—in particular an anesthetic agent such as Propofol or a substance relating to an anesthetic agent such as Propofol—on the catheter tube 10 of an endo-tracheal catheter 1, in an embodiment shown in FIG. 2 an insert tube 13 is received within an inner lumen 102 of a tubular wall 101 of the catheter tube 10. The insert tube 13 prevents a direct contact of a gaseous flow guided through the catheter tube 10 by means of a flow channel defined by and extending through the insert tube 13 with the tubular wall 101 of the catheter tube 10, such that adsorption of substances of the gaseous flow on the tubular wall 101 cannot take place or at least is reduced.

The insert tube 13 is made from a material exhibiting characteristics of reduced adsorption of a substance of interest, in particular an anesthetic agent such as Propofol. The insert tube 13 may in particular be made from a material such as PTFE, PFA, FEP, PEEK or the like and hence may exhibit a characteristic of a generally reduced adsorption of substances.

In contrast, the tubular wall 101 of the catheter tube 10 may be made for example of a PVC material and hence may be produced in a cost-effective manner.

The insert tube 13 is received within the inner lumen 102 of the catheter tube 10 and for example is in close abutment with the inner face of the tubular wall 101. The insert tube 13 has for example a wall thickness of 0.5 mm or less and hence essentially does not reduce the cross-sectional area of the inner lumen 102 of the catheter tube 10 and does not substantially impact resistance for the gaseous flow through the catheter tube 10.

The insert tube 13 fully extends through the catheter tube 10 from a first end 104 of the catheter tube 10, at which the tubular wall 101 is connected to the connection piece 11 of the endo-tracheal catheter 1, to a second, far end 105 which is to be inserted into the trachea 40 of the patient 4, as it is visible in FIG. 1. A distal end 132 of the insert tube 13 herein comes to rest at the far end 105 of the catheter tube 10, whereas a proximal end 130 extends through a catheter tube opening 100 at which the catheter tube 10 opens into a chamber 112 defined by the connection piece 11 and protrudes from the first end 104 of the catheter tube 10 into the chamber 112. The proximal end 130 in this way reaches towards a port 110 at which a side-stream line 12 is connected to the connection piece 11.

To axially fix the insert tube 13 with respect to the catheter tube 10 in order to prevent the insert tube 13 to axially move into and through the catheter tube 10 towards the patient 4, a stop element 131 in the shape of a sleeve is placed on the proximal end 130 of the insert tube 13, as this is shown in FIG. 2. Because the stop element 131, which circumferentially surrounds the proximal end 130, has a diameter larger than the diameter of the inner lumen 102 of the catheter tube 10, the stop element 131 may not move into the inner lumen 102 and, because it axially is fixed on the proximal end 130 of the insert tube 13, axially secures the insert tube 13 with respect to the catheter tube 10.

The side-stream line 12, with a side-stream line opening 120, opens into the chamber 112 of the connection piece 11, the side-stream line opening 120 being in close proximity to the tip of the proximal end 130 of the insert tube 13 at which the insert tube 13 opens into the chamber 112. Because the proximal end 130 and the side-stream line opening 120 of the side-stream line 12 are located in close proximity to each other, a gas probe may be taken via the side-stream line 12 from a gaseous flow flowing through the insert tube 130 and through the chamber 112 of the connection piece 11 in order to measure a concentration of a substance of interest in the gaseous flow, without adsorption on housing walls 111 of the connection piece 11 substantially impacting the accuracy of the measurement.

The side-stream line 12 serves to connect a detection device 2 (FIG. 1) in the shape of a gas detector suitable to detect and measure a concentration of a substance of interest in the gaseous flow in a continuous or periodic fashion to the connection piece 11. The side-stream line 12 may, similar to the insert tube 13, be made from a material exhibiting characteristics of reduced adsorption for a substance of interest, for example a material comprising PTFE, PFA, FEP, PEEK or the like.

Because the insert tube 13 prevents adsorption on the tubular wall 101 of the catheter tube 10 and because adsorption on the side-stream line 12 is reduced to a minimum level and in addition due to the close proximity of the side-stream line opening 120 of the side-stream line 12 to the proximal end 130 of the insert tube 13, adsorption effects may not substantially impact and deteriorate measurement results of the detection device 2.

Because the side-stream line 12 with its side-stream line opening 120 reaches towards the center of the chamber 112 of the connection piece 11, furthermore the risk that moisture enters into the side-stream line 12 is reduced.

The catheter tube 10, at its first end 104, is connected to a bottom end 113 of the connection piece 11. At a top end 114 a filter 32 of a ventilation system 3 may be connected to the connection piece 11, as this is indicated in FIG. 1.

In an alternative embodiment, as illustrated in FIG. 3, instead of using an insert tube 13, a coating 103 in the shape of a layer of a material exhibiting characteristics of reduced adsorption of a substance of interest may be placed on the inside of the tubular wall 101 of the catheter tube 10, the coating 103 preventing direct contact of the gaseous flow flowing through the inner lumen 102 of the catheter tube 10 with the tubular wall 101 and hence preventing adsorption on the tubular wall 101.

Likewise, the side-stream line 12 may comprise a coating of this kind, such that the side-stream line 12 may be made from a material such as a PVC material, adsorption being prevented by a coating covering the side-stream line 12 on the inside.

A coating 103 of this kind may for example be formed by deposition of a suitable material, such as a sapphire (SiOx) material, to form a thin layer on the inside of the tubular wall 101 of the catheter tube 10 or on the inside of the side-stream line 12.

Alternatively, the catheter tube 10 and/or the side-stream line 12 may be formed as multi-layered tubes for example using a co-extrusion process. In this way the catheter tube 10 and/or the side-stream line 12 may be formed as tubes having an outer tube wall made for example from a PVC material and an inner tube wall (representing an inner coating) for example made from or comprising a material such as PTFE (polytetrafluoroethylene), PFA (perfluoralkoxy polymer), FEP (perfluor(ethylene-propylene)), or PEEK (polyether ether ketone), i.e., a material generally exhibiting reduced adsorption characteristics in particular for an anesthetic agent such as Propofol.

The idea of the invention shall not be limited by the embodiments described above, but rather may be implemented also in an entirely different fashion.

For example, an insert tube and a coating of the type described above may also be used in combination. For example, a coating may also be placed on the insert tube in order to prevent adsorption on the insert tube.

An endo-tracheal catheter of the type described above may be used within an anesthesia procedure, but may also be used in a different clinical context in order to detect and measure the presence of a substance in a gaseous flow.

LIST OF REFERENCE NUMERALS

1 Endo-tracheal catheter
10 Catheter tube
100 Cather tube opening
101 Tubular wall
102 Inner lumen (Channel)
103 Coating
104 First end
105 Second end
11 Connection piece
110 Port
111 Housing wall
112 Chamber
113 Bottom end
114 Top end
12 Side-stream line
120 Side-stream line opening
13 insert tube
130 Proximal end
131 Stop element (sleeve)
132 Distal end
2 Detection device
3 Ventilation system
30 Ventilator
31 Filter
32 Ventilation lines
4 Patient
40 Trachea
41 lungs

The invention claimed is:

1. An endo-tracheal catheter for use in an anesthetic procedure, comprising:
   a catheter tube to be inserted into the trachea of a patient, the catheter tube having a tubular wall defining an inner lumen for guiding a gaseous flow, and
   a connection piece which defines a chamber being in fluid connection with the catheter tube and comprising a port for connecting a detection device to the endo-tracheal catheter for detecting at least one substance in the gaseous flow flowing through the catheter tube,
   wherein either an insert tube received in the inner lumen of the catheter tube for guiding the gaseous flow through the catheter tube extends through the catheter tube from a first end of the catheter tube, at which the tubular wall is connected to the connection piece of the endo-tracheal catheter, to a second, far end of the catheter tube which is to be inserted into the trachea of the patient, and/or a coating covers the tubular wall of the catheter tube at a side facing the inner lumen for guiding the gaseous flow through the catheter tube,
   wherein the insert tube comprises a proximal end, the proximal end comprising a tip at which the insert tube opens into the chamber;
   wherein the insert tube further comprises a stop element fixed to the proximal end, the stop element being constituted to prevent the proximal end to axially move into the inner lumen of the catheter tube.

2. An endo-tracheal catheter according to claim 1, wherein the insert tube and/or the coating are made from a material different than the tubular wall of the catheter tube.

3. An endo-tracheal catheter according to claim 1, wherein the insert tube and/or the coating are made from a material providing for a reduced adhesion of said substance to be detected by said detection device as compared to the tubular wall of the catheter tube.

4. An endo-tracheal catheter according to claim 1 wherein the tubular wall is made from PVC.

5. An endo-tracheal according to claim 1 wherein the insert tube is made from polytetrafluoroethylene, perfluoralkoxy polymer, perfluor(ethylene-propylene), or polyether ether ketone.

6. An endo-tracheal according to claim 1 wherein the insert tube has a wall thickness of 0.5 mm or less.

7. An endo-tracheal according to claim 1 the proximal end of the insert tube reaching into the chamber and protruding from an opening of the catheter tube at which the catheter tube opens into the chamber of the connection piece.

8. An endo-tracheal according to claim 7, wherein the proximal end extends, from said catheter tube opening of the catheter tube, towards the port such that the insert tube opens into the chamber at a location in the vicinity of the port.

9. Endo-tracheal catheter according to claim 1 wherein the coating is made from SiOx.

10. An endo-tracheal according to claim 1 wherein the coating comprises a thickness of less than 10 μm, or less than 5 μm.

11. An endo-tracheal catheter according to claim 1 wherein the coating is formed by co-extrusion together with the tubular wall of the catheter tube.

12. An endo-tracheal catheter according to claim 1 wherein a side-stream line is connected to the port for connecting said detection device to the endo-tracheal catheter.

13. An endo-tracheal catheter according to claim 12, wherein the side-stream line reaches into the chamber and protrudes from a housing wall of the connection piece defining the chamber.

14. An endo-tracheal catheter according to claim 12 wherein the side-stream line is at least partially made from polytetrafluoroethylene, perfluoralkoxy polymer, perfluor(ethylene-propylene), or polyether ether ketone.

15. A system, wherein an endo-tracheal catheter according to claim 1 and a ventilation system having ventilator being in fluid connection with the connection piece of the endo-tracheal catheter.

16. An endo-tracheal catheter according to claim 1 wherein the stop element circumferentially surrounds the proximal end of the insert tube and has a diameter larger than the diameter of the inner lumen.

\* \* \* \* \*